(12) United States Patent
Zhang et al.

(10) Patent No.: US 8,003,408 B2
(45) Date of Patent: Aug. 23, 2011

(54) MODIFICATION OF METAL NANOPARTICLES FOR IMPROVED ANALYTE DETECTION BY SURFACE ENHANCED RAMAN SPECTROSCOPY (SERS)

(75) Inventors: Jingwu Zhang, San Jose, CA (US); Narayan Sundararajan, San Francisco, CA (US); Sarah M. Ngola, Sunnyvale, CA (US); Handong Li, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 415 days.

(21) Appl. No.: 11/319,747

(22) Filed: Dec. 29, 2005

(65) Prior Publication Data
US 2007/0155021 A1 Jul. 5, 2007

(51) Int. Cl.
*G01N 33/553* (2006.01)
*G01N 33/20* (2006.01)
*G01N 21/00* (2006.01)
*A61K 9/54* (2006.01)

(52) U.S. Cl. ............ 436/525; 436/75; 436/80; 436/164; 424/490

(58) Field of Classification Search .................. 436/524, 436/525, 80, 78, 164; 977/773; 424/490
See application file for complete search history.

(56) References Cited

U.S. PATENT DOCUMENTS

| | | | |
|---|---|---|---|
| 6,479,146 B1 * | 11/2002 | Caruso et al. ................. | 428/403 |
| 2005/0148098 A1 * | 7/2005 | Su et al. ........................ | 436/518 |
| 2006/0073336 A1 * | 4/2006 | Zhang et al. .................. | 428/407 |
| 2006/0105052 A1 * | 5/2006 | Acar et al. .................... | 424/490 |

OTHER PUBLICATIONS

Bhattacharya et al. Synthesis and characterizaiton of novel tationic lipid and cholesterol coated gold nanoparticles and their interaction with dipalmatoylphosphatidylcholine membrane. Langmuir 2003, vol. 19, pp. 4439-4447.*

Cliffel et al. Mercaptoammonium-monolayer-protected, water soluble gold, silver and palladium clusters. Langmuir 2000, vol. 16, pp. 9699-9702.*

Kumar et al. Linear superclusters of colloidal gold particles by electrostatic assembly on DNA templates. Adv. Mater. 2001, vol. 13, No. 5, pp. 341-344.*

Maruyama and Futamata, "Elastic scattering and emission correlated with single-molecule SERS," Journal of Raman Spectroscopy, 2005; 36 (6-7): 581-592.

Wang and Li, "Surfactant-Aided Surface-Enhanced Resonance Raman Spectroscopic Study of Some Anionic Dye Molecules," Journal of Raman Spectroscopy, 1996; 27 (5): 385-389.

(Continued)

*Primary Examiner* — Shafiqul Haq
(74) *Attorney, Agent, or Firm* — Pillsbury Winthrop Shaw Pittman LLP

(57) ABSTRACT

A SERS active particle having a metal-containing particle and a cationic coating on the metal-containing particle, wherein the SERS active particle carries a positive charge is disclosed. Also, a SERS active particle having a metal-containing particle and a non-metallic molecule, wherein the metal-containing particle is derivatized with the non-metallic molecule is disclosed. In addition, several methods of modifying the nanoparticles surfaces of a SERS active particle and of improving the interaction between the SERS active particle and an analyte are disclosed.

9 Claims, 8 Drawing Sheets

OTHER PUBLICATIONS

Kuo and Chen, "Formation of Silver Nanoparticles under Structured Amino Groups in Pseudo-dendritic Poly (allylamine) Derivatives," J. Phys. Chem. B, 2003; 107 (41): 11267-11272.

Kim et al., "Silver-Particle-Based Surface-Enhanced Raman Scattering Spectroscopy for Biomolecular Sensing and Recognition," Langmuir, 2006; 22 (7): 3421-3427.

Wei et al., "DNA-Network-Templated Self-Assembly of Silver Nanoparticles and Their Application in Surface-Enhanced Raman Scattering," J. Phys. Chem. B, 2005; 109 (50): 23941-23947.

Office Action in related Taiwanese Application No. 95146922 dated Feb. 2, 2010.

Maruyama Y et al., "Elastic Scattering and emission correlated with single-molecules SERS", Journal of Raman Spectroscopy, vol. 26, No. 6-7, pp. 581-592, Jun. 2005.

Wang K et al., "Surfactant-Aided Surface-Enhanced Resonance Raman Spectroscopic Study of Some Anionic Dye Molecules", Journal of Raman Spectroscopy, vol. 27, No. 5, pp. 385-389, May 1996.

* cited by examiner

MODIFICATION OF METAL NANOPARTICLES FOR IMPROVED ANALYTE DETECTION BY SURFACE ENHANCED RAMAN SPECTROSCOPY (SERS)

RELATED APPLICATIONS

This application is related to U.S. patent application Ser. No. 10/814,695, filed Mar. 30, 2004, entitled "Surface Modification of Metals for Biomolecules Detection Using Surface Enhanced Raman Scattering (SERS)," U.S. patent application Ser. No. 10/748,336, filed Dec. 29, 2003, entitled "Composite Organic-Inorganic Nanoparticles (COIN) as SERS Tags for Analyte Detection," U.S. patent application Ser. No. 10/916,710, filed Aug. 11, 2004, entitled "Multiplex Detection of Analytes in Fluid Systems," U.S. patent application Ser. No. 10/927,996, filed Aug. 26, 2004, entitled "Biomolecule Analysis Using Raman Surface Scanning", and U.S. patent application Ser. No. 11/027,470, filed Dec. 30, 2004, entitled "Biomolecule Analysis Using Raman Surface Scanning," which are incorporated herein by reference.

FIELD OF INVENTION

The ability to detect and identify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity. Compared to a fluorescent spectrum that normally has a single peak with half peak width of tens of nanometers to hundreds of nanometers, a Raman spectrum has multiple bonding-structure-related peaks with half peak width of as small as a few nanometers.

Among many analytical techniques that can be used for chemical structure analysis, Raman spectroscopy SERS technology is attractive for its capability to provide rich structure information from a small optically-focused area or detection cavity. The technology uses, for example, DNA gene probes based on SERS labels for gene detection and DNA mapping. Some of the detection methods use nanostructured metallic substrates, typically particles, as SERS-active platforms. The surface-enhanced Raman gene (SERGen) probes can be used to detect DNA targets via hybridization to DNA sequences complementary to these probes. The probes do not generally require the use of radioactive labels and have great potential to provide both sensitivity and selectivity.

Furthermore, SERS techniques make it possible to obtain a $10^6$ to $10^{14}$ fold Raman signal enhancement as compared to the Raman signal from a molecule without the enhancement provided by SERS techniques, and may even allow for single molecule detection sensitivity. Such huge enhancement factors are attributed primarily to enhanced electromagnetic fields on curved surfaces of metals deposited on particles used for SERS techniques. Such enhancement factors have also been observed on sharp edges and at the junctions between aggregates. Although the electromagnetic enhancement (EME) has been shown to be related to the roughness of metal surfaces or particle size when individual metal colloids are used, SERS is generally most effectively detected from aggregated colloids.

As a result of the advantages of SERS, there has been considerable interest in using SERS for detection of biomolecules, particularly due to its great sensitivity and low detection limit. Single-molecule detection has been achieved for certain compounds such as Adenine and Rhodamine 6G (R6G). However, there is still a need to future improve the sensitivity of the technique for a vast majority of molecules. It is believed that the strong enhancement by SERS primarily results from the magnification of electromagnetic field near the surface of certain metal particles such as silver and gold. However, the electromagnetic enhancement decays drastically with increasing distance from the surface. Therefore, to achieve strong enhancement, it is important to bring the molecules as close as possible to the surface. Molecules with very low absorption affinity for the substrate providing enhancement by SERS could therefore have low SERS signals.

Silver and gold colloidal particles have been used as preferred substrates for the particles used for SERS techniques. However, the nanoparticles or nanoclusters that typically form the SERS active particles are generally prepared by commonly employed methods that result in the SERS active particles to carry negative charges on the surface of the SERS active particles. Thus, analytes which possess one or more negative charges usually have relatively low SERS signal as compared with similar cationic molecules. The embodiments of the invention present several approaches to modify the substrate surface of the SERS active particles in order to facilitate analyte absorption and thereby bring the molecules as close as possible to the surface of the SERS active particles.

BRIEF DESCRIPTION OF THE DRAWINGS

FIG. 6 shows the surface of silver particle completely covered with silica as revealed by TEM.

DETAILED DESCRIPTION

Figure 1:
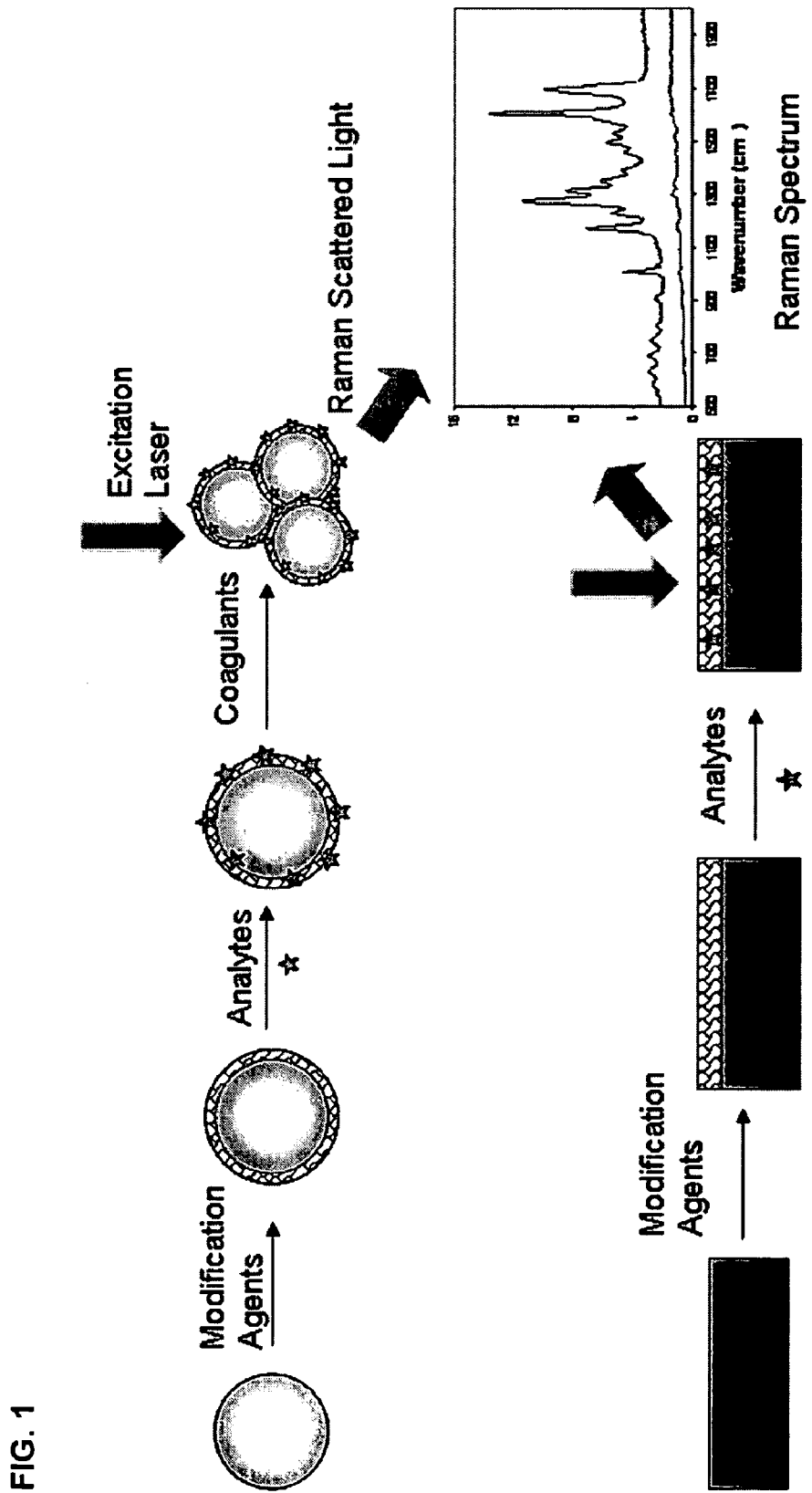
FIG. 1 shows the steps involved for obtaining Raman spectra of analytes by modifying SERS nanoparticles (top view) and surfaces (bottom view).

This invention relates to positively charges SERS active particles, which are generally nanoparticles or nanoclusters, and to methods to make positively charged nanoparticles/ nanoclusters or to make the negatively charged nanoparticles/ nanoclusters positive. In addition, hydrophobic and specific interactions including covalent binding between the analytes and modified surface are also explored to improve the SERS signals of different types of analytes.

A biological sample often contains many thousands or even more types of biomolecules and clinical diagnosis needs to measure multiple analytes for disease confirmation. Currently, the same type of nanoparticles is used to detect all kinds of analyte molecules regardless of their molecular structure. The detection limit or a given analyte is improved by optimizing the quality of silver particles during particle preparation. The embodiments of the invention allow for the SERS nanoparticles or nanoclusters to be modified according to the nature of analytes to produce a higher signal intensity and lower detection limit than previously possible using the same type of SERS nanoparticles or nanoclusters. The embodiments of the invention would also allow for multiple analyte detection from a single sample and a single test, which could be of great interest to clinical diagnosis, and biomedical research as well.

Analytes include nucleic acids (DNA and RNA), which can form double-stranded molecules by hybridization, that is, complementary base pairing. The specificity of nucleic acid hybridization is such that the detection of molecular and/or nanomaterials binding events can be done through electrical readout of polarization changes caused by the interaction of charged target molecules (DNA, RNA, proteins, for example.) and chemically modified nanomaterials (carbon nanotubes, nanowires, nanoparticles functionalized with DNA, for example) with complementary molecular probes (DNA, RNA, anti-body, for example) attached to the electrodes (such as Au, Pt, for example). This specificity of complementary base pairing also allows thousands of hybridization to be carried out simultaneously in the same experiment on a DNA chip (also called a DNA array).

Molecular probes are immobilized on the surface of individually addressable electrode arrays through the surface functionalization techniques. Electrodes allow polarization changes to be electrically detected. The polymer arrays of the embodiment of the invention could be a DNA array (collections of DNA probes on a shared base) comprising a dense grid of spots (often called elements or pads) arranged on a miniature support. Each spot could represent a different gene.

The probe in a DNA chip is usually hybridized with a complex RNA or cDNA target generated by making DNA copies of a complex mixture of RNA molecules derived from a particular cell type (source). The composition of such a target reflects the level of individual RNA molecules in the source. The intensities of the signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte", "target" or "target molecule" refers to a molecule of interest that is to be analyzed and can be any molecule or compound. The analyte may be a Raman active compound or a Raman inactive compound. Further, the analyte could be an organic or inorganic molecule. Some examples of analytes may include a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The analyte molecule may be fluorescently labeled DNA or RNA.

An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The term analyte further includes polynucleotide analytes such as those polynucleotides defined below. These include m-RNA, r-RNA, t-RNA, DNA, DNA-RNA duplexes, etc.

The term analyte also includes receptors that are polynucleotide binding agents, such as, for example, peptide nucleic acids (PNA), restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

The analyte can further be a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fingus, protozoan, or virus. Also, the analyte could be charged. A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Bioanalyte can also be complex of molecules or compounds in organized or random fashion, such cells, virus, bacteria, fungi, etc.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "capture molecule" refers to a molecule that is immobilized on a surface. The capture molecule is generally, but not necessarily, binds to a target or target molecule. The capture molecule is typically a nucleotide, an oligonucleotide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

The term "bi-functional linker group" refers to an organic chemical compound that has at least two chemical groups or moieties, such are, carboxyl group, amine group, thiol group, aldehyde group, epoxy group, that can be covalently modified specifically; the distance between these groups is equivalent to or greater than 5-carbon bonds.

The terms "die," "polymer array chip," "DNA array," "array chip," "DNA array chip," "bio-chip" or "chip" are used interchangeably and refer to a collection of a large number of probes arranged on a shared substrate which could be a portion of a silicon wafer, a nylon strip or a glass slide.

The term "molecule" generally refers to a chemical made up of two or more atoms and includes a macromolecule, biomolecule or polymer as described herein. However, arrays comprising single molecules, as opposed to macromolecules or polymers, are also within the scope of the embodiments of the invention. The term "biomolecule" refers to any organic molecule that is part of a living organism. A "complex of a biomolecule" refers to a structure made up of two or more types of biomolecules. Examples of a complex of biomolecule include a cell or viral particles. A cell can include bacteria, fingi, animal mammalian cell, for example.

An "activating group" refers to those groups which, when attached to a particular chemical functional group or reactive site, render that site more reactive toward covalent bond formation with a second chemical functional group or reactive site.

A "polymeric brush" ordinarily refers to polymer films comprising chains of polymers that are attached to the surface of a substrate. The polymeric brush could be a functionalized polymer films which comprise functional groups such as hydroxyl, amino, carboxyl, thiol, amide, cyanate, thiocyanate, isocyanate and isothio cyanate groups, or a combination thereof, on the polymer chains at one or more predefined regions. The polymeric brushes of the embodiment of the invention are capable of attachment or stepwise synthesis of macromolecules thereon.

A "linker" molecule refers to any of those molecules described supra and preferably should be about 4 to about 40 atoms long to provide sufficient exposure. The linker molecules may be, for example, aryl acetylene, ethylene glycol oligomers containing 2-10 monomer units, diamines, diacids, amino acids, among others, and combinations thereof. Alternatively, the linkers may be the same molecule type as that being synthesized (i.e., nascent polymers), such as polynucleotides, oligopeptides, or oligosaccharides.

"Monomer" as used herein refers to those monomers that are used to a form a polymer. However, the meaning of the monomer will be clear from the context in which it is used. The monomers in a given polymer or macromolecule can be identical to or different from each other. A monomer can be a small or a large molecule, regardless of molecular weight. Furthermore, each of the monomers may be protected members which are modified after synthesis.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-500 nanometer range. Preferably, a nanomaterial has properties and functions because of the size and can be manipulated and controlled on the atomic level. Examples of nanomaterials include nanoparticles, carbon nanotube and fullerene. A "carbon nanotube" refers to a fullerene molecule having a cylindrical or toroidal shape. A "fullerene" refers to a form of carbon having a large molecule consisting of an empty cage of sixty or more carbon atoms.

A "nanoparticle" is a microscopic particle whose size is measured in nanometers. It is defined as a particle with at least one dimension <100 nm. Nanoparticles made of semiconducting material are also labeled quantum dots. Nanoparticles are of great scientific interest as they are effectively a bridge between bulk materials and atomic or molecular structures. A bulk material should have constant physical properties regardless of its size, but at the nano-scale this is often not the case. Nanoparticles often demonstrate size-dependent properties are observed such as quantum confinement in semiconductor particles, surface plasmon resonance in some metal particles and supermagnetism in magnetic materials. At the small end of the size range, nanoparticles are often referred to as nanoclusters. Metal, dielectric and semiconductor nanoparticles could be formed, as well as hybrid structures (e.g., core-shell nanoparticles). Nanospheres, nanorods, and nanocups are just a few of the shapes that have been grown. Semiconductor quantum dots and nanocrystals are types of nanoparticles. Such nanoscale particles are used in biomedical applications as drug carriers or imaging agents.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers".

An "oligonucleotide" is a polynucleotide having 2 to 20 nucleotides.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

An "antibody" is any of various bodies or substances in the blood which act in antagonism to harmful foreign bodies, as toxins or the bacteria producing the toxins. Normal blood serum apparently contains various antibodies, and the introduction of toxins or of foreign cells also results in the development of their specific antibodies. For example, an antibody is a Y-shaped protein on the surface of B cells that is secreted into the blood or lymph in response to an antigenic stimulus, such as a bacterium, virus, parasite, or transplanted organ, and that neutralizes the antigen by binding specifically to it; an immunoglobulin.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, fuiction, and regulation of the body's cells, tissues, and organs, and each protein has unique functions. Examples are hormones, enzymes, and antibodies.

A "carbohydrate" is a compound with carbon, hydrogen and oxygen usually in a proportion to form water with the general formula $C_n(H_2O)_n$. Carbohydrates can also be called chemically as neutral compounds of carbon, hydrogen and oxygen. Carbohydrates are mainly sugars and starches, together constituting one of the three principal types of nutrients used as energy sources (calories) by the body. Carbohydrates come in simple forms such as sugars and in complex forms such as starches and fiber. The body breaks down most sugars and starches into glucose, a simple sugar that the body can use to feed its cells. Complex carbohydrates are derived from plants. Dietary intake of complex carbohydrates can lower blood cholesterol when they are substituted for saturated fat. Carbohydrates are classified into mono, di, tri, poly and heterosaccharides. The smallest carbohydrates are monosaccharides such as glucose whereas polysaccharides such as starch, cellulose and glycogen can be large and even indeterminate in length.

A "lipid" is defined as a substance such as a fat, oil or wax that dissolves in alcohol but not in water. Lipids contain carbon, hydrogen and oxygen but have far less oxygen proportionally than carbohydrates. Lipids are an important part of living cells. Together with carbohydrates and proteins, lipids are the main constituents of plant and animal cells. Cholesterol and triglycerides are lipids. Lipids are easily stored in the body. They serve as a source of fuel and are an important constituent of the structure of cells. Lipids include fatty acids, neutral fats, waxes and steroids (like cortisone). Compound lipids (lipids complexed with another type of chemical compound) comprise the lipoproteins, glycolipids and phospholipids.

An "antigen" a substance that is capable of causing the production of an antibody. For example, when an antigen is introduced into the body, it stimulates the production of an antibody. Antigens include toxins, bacteria, foreign blood cells, and the cells of transplanted organs.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g., opiates, steroids, etc.), lectins, sugars, polynucleotides, nucleic acids, oligosaccharides, proteins, and monoclonal antibodies. Ligands to cells or cell-derived molecules, which can include both known and unknown ligands as well as putative drug candidates that are either unattached to other solid supports or attached to surfaces or particle-like structures, could interact with other cell-derived molecules in a manner such that binding between two binding partners occurs and can be detected. One of the binding partners or its attached support can additionally be derivatized with a substance that can be recognized and quantified by a detection apparatus. This complex (through interaction) is then brought into the presence of the detection apparatus using characteristics of the associated complex that differentiate it from the unassociated binding partners.

An "affinity binding partner" or "binding partner" could be a probe or a ligand defined above.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. However, as the term receptor is used herein, no difference in meaning is intended. A "ligand receptor pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

"Specific binding" or "specific interaction" is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide hybridization interactions, and so forth.

"Non-specific binding" or "non-specific interaction" is non-covalent binding between molecules that is relatively independent of specific surface structures. Non-specific binding may result from several factors including hydrophobic interactions between molecules.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes can have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes can generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term "reporter" means a detectable moiety. The reporter can be detected, for example, by Raman spectroscopy. Generally, the reporter and any molecule linked to the reporter can be detected without a second binding reaction. The reporter can be COIN (composite-organic-inorganic nanoparticle), magnetic-COIN, quantum dots, and other Raman or fluorescent tags, for example.

The phrase "SERS active material" or "SERS active particle" refers to a material or a particle that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides a greatly enhanced Raman signal from Raman-active analyte molecules that have been adsorbed onto certain specially-prepared SERS active surfaces. The SERS active surface could be planar or curved. Typically, the SERS active surfaces are metal surfaces. Increases in the intensity of Raman signal could be in the order of $10^4$-$10^{14}$ for some systems. SERS active material or particle includes a variety of metals including coinage (Au, Ag, Cu), alkalis (Li, Na, K), Al, Pd and Pt. In the case of SERS active particle, the particle size of SERS active particles could range from 1 to 5000 nanometers, preferably in the range of 5 to 250 nanometers, more preferably in the range of 10 to 150 nanometers, and most preferably 40 to 80 nanometers. In one embodiment, there are provided methods for producing metallic colloids to produce SER active material or particles. Such methods can be performed, for example, by mixing metal cations with a reducing agent in aqueous solution, and heating the aqueous solution to about 95° C., thereby producing metallic colloids.

As used herein, the term "colloid" refers to nanometer size metal particles suspending in a liquid, usually an aqueous solution. In the methods of the invention, the metal cations and reducing agent are mixed in aqueous solution prior to heating. This method results in a 50% enhancement of SERS signals obtained from such colloids, and also results in an increase in reproducibility from 10-20% to 80-100%. Typical metals contemplated for use in the practice of the invention include, for example, silver, gold, platinum, copper, aluminum, and the like. A variety of reducing agents are contemplated for use in the practice of the invention, such as for example, citrate, borohydride, and the like. Sodium citrate is used in certain embodiments of the invention. Typically, the metal cations and reducing agent are each present in aqueous solution at a concentration of at least about 0.5 mM. After mixing the metal cations and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof. The methods for producing metallic colloids described herein are in contrast to prior methods wherein a boiling silver nitrate solution is titrated with a sodium citrate solution. This titration method can produce only one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

The term "COIN" refers to a composite-organic-inorganic nanoparticle(s). The COIN could be surface-enhanced Raman spectroscopy (SERS)-active nanoparticles incorporated into a gel matrix and used in certain other analyte separation techniques described herein. These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoparticles include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoparticles containing Raman-active organic compounds of different structures, mixtures, and ratios. Thus, the methods described herein employing COINs are useful for the simultaneous detection of many analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoparticles described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. This COIN can typically be isolated by membrane filtration. In addition, COINs of different sizes can be enriched by centrifugation.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

SERS active particles or COINs may be used to detect the presence of a particular target analyte, for example, a nucleic acid, oligonucleotide, protein, enzyme, antibody or antigen. The nanoparticles may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoparticles.

Also, SERS-active particles or COINs that have an antibody as binding partner could be used to detect interaction of the Raman-active antibody labeled constructs with antigens either in solution or on a solid support. It will be understood that such immunoassays can be performed using known methods such as are used, for example, in enzyme-linked immunosorbent assays (ELISA), Western blotting, or protein arrays, utilizing a SERS-active particle or COIN having an antibody as the probe and acting as either a primary or a secondary antibody, in place of a primary or secondary antibody labeled with an enzyme or a radioactive compound. In another example, a SERS-active particle or COIN is attached to an enzyme probe for use in detecting interaction of the enzyme with a substrate.

Another group of exemplary methods could use the SERS-active particles or COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active particle or COIN. Detection of the specific Raman label in the SERS-active particle or COIN identifies the nucleotide sequence of the oligonucleotide probe, which in turn provides information regarding the nucleotide sequence of the target polynucleotide.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "oxidation" means losing electron to oxidize. The term "reduction" means gaining electrons to reduce. The term "redox reaction" refers to any chemical reaction which involves oxidation and reduction.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "fluid" used herein means an aggregate of matter that has the tendency to assume the shape of its container, for example a liquid or gas. Analytes in fluid form can include fluid suspensions and solutions of solid particle analytes.

The term "derivatize" means to alter the chemical composition of a molecule by a chemical reaction which changes some part of the molecule, and preferably leaving most of the molecule unchanged.

Embodiments of the invention relate to a method of obtaining metal particles that can be used for detection of a wide range of analytes by surfaced enhanced Raman spectroscopy (SERS). The embodiments of the invention allow for various ways to create layers of additional compounds (including simple ions, small molecules, polymers and even nanoparticles) on the SERS substrate to increase adsorption of analyte and thus its signal intensity. Electrostatic, hydrophobic, covalent and other specific interactions between the analyte molecules and the substrate surface are preferably considered in selecting the surface modification approaches.

The embodiments of invention include a method of preparing nanoparticles or nanoclusters with modified layers of compounds that facilitate the adsorption of analyte for surface enhanced Raman spectroscopy analysis. The method could comprises the synthesizing silver and gold particles of average size in the range of 20-100 nm and modifying the nanoparticle surfaces by one or more of the following methods, for example: (1) Reversing the particle charges by adsorption of simple molecules, polyelectrolytes and nanoparticles; (2) coating the metal particles with a layer of inorganic materials which facilitate analyte adsorption or can be further modified for that purpose; (3) coating the substrate with materials which retain analyte molecules by hydrophobic interaction; and (4) derivatizing the substrate with ligands or macromolecules which have high affinity for the analytes (including covalent binding, H-bonding, antibody-antigen interaction).

The embodiments of the invention relate to a material comprising a SERS active substance comprising a metal and a cationic coating on the material such that the material carries a positive charge. Preferably, the SERS active substance is located on a surface of the material and comprises metallic colloids. In some embodiments of the invention, the material has planar surface (e.g., sheets, ribbons, flakes, electrodes) or a curved surface (e.g., nanoparticles, spherical particles). Preferably, the cationic coating comprises an adsorbed additive or a deposited additive. More preferably, the adsorbed additive comprises a material selected from the group consisting of ions, a thiol-containing compound, a polymer and nanoparticles. In one variation, the deposited additive comprises a layer of an organic material or an inorganic material. Preferably, the nanoparticles comprise an iron-containing material. More preferably, the layer of organic material comprises a cationic polymer. In some variations, the layer of inorganic material comprises silica, hematite or titanium oxide. Preferably, the layer of organic material comprises a polymer having a positively charged functional group.

Other embodiments of the invention relate to a material comprising (1) a SERS active substance comprising a metal and (2) a non-metallic molecule, wherein the SERS active substance is attached to the non-metallic molecule. Preferably, the SERS active substance is located on a surface of the material. More preferably, the SERS active substance comprises metallic colloids. Preferably, the metal-containing particle comprises a metal selected from the group consisting of silver, gold, platinum, iron, an oxide of iron, aluminum, an oxide of aluminum and combinations thereof. Preferably, the non-metallic molecule is selected from the group consisting of a thiol-containing compound, a ligand, an antigen, an antibody, an oligo-nucleic acid, a reactive molecule adapted to form a covalent bond with an analyte, and combinations thereof. Preferably, the ligand is selected from the group consisting of an immobilized metal affinity chromatography (IMAC) for a protein or a phosphoprotein, glutathione, a boronic acid, a lectin and combinations thereof. More preferably, the reactive molecule is selected from N-Hydroxysuccinimide ester, isothiocyanate, sulfonyl halide, maleimide, thiol, haloacetyl and combinations thereof.

Yet other embodiments of the invention relate to a SERS active particle comprising a metal-containing particle and a cationic coating on the metal-containing particle, wherein the SERS active particle carries a positive charge. Preferably, the metal-containing particle comprises metallic colloids. Preferably, the cationic coating comprises an adsorbed additive or a deposited additive. More preferably, the adsorbed additive comprises a material selected from the group consisting of ions, a thiol-containing compound, a polymer and nanoparticles. In one variation, the deposited additive comprises a layer of an organic material or an inorganic material. More preferably, the thiol-containing compound comprises a thiolamine. Also, more preferably, the nanoparticles comprise an iron-containing material and the layer of organic material comprises polyethylene amine. Preferably, the layer of organic material comprises a cationic polymer. Preferably, the layer of inorganic material comprises silica, hematite or titanium oxide. In one variation, the layer of organic material comprises a polymer having a positively charged functional group.

Other embodiments of the invention relate to a SERS active particle comprising a metal-containing particle and a non-metallic molecule, wherein the metal-containing particle is attached to the non-metallic molecule. Preferably, the non-metallic is attached to the non-metallic molecule by covalent bonding, by adsorption or by derivatization. Preferably, the non-metallic molecule comprises a reactive group. More preferably, the non-metallic molecule comprises a ligand selected from the group consisting of $TiO_2$, a tagged protein, a phosphoprotein, a boronic compound, and a lectin Yet other embodiments of the invention relate to a complex comprising a SERS active particle comprising a metal-containing particle and an analyte comprising a compound carrying a positive charge. Preferably, the analyte is bonded to the SERS active particle and the compound carries the positive charge before the analyte is bonded to the SERS active particle. The complex could further comprise a reactive molecule or a polymer bonded to the metal-containing particle the analyte. Preferably, the reactive molecule comprises a reactive group selected from the group consisting of NHS ester, isothiocyanate, sulfonyl halide, maleimide, thiol, haloacetyl and combinations thereof. Preferably, the analyte is a thiol-containing compound, an amine-containing compound, or combinations thereof.

Yet, other embodiments of the invention relate to a method comprising contacting metal ions with a reducing agent to form metal-containing nanoparticles or nanoclusters and modifying a surface of the metal-containing nanoparticles or nanoclusters such that the surface carries a positive charge. Preferably, the modifying the surface comprises adsorbing an additive on the surface. Preferably, the additive comprises a material selected from the group consisting of positively charged ions, a thiol-containing compound, a polymer and nanoparticles. Preferably, the metal-containing nanoparticles or nanoclusters comprise silver particles and the polymer is polyallylamine or polyamonium. Preferably, the metal-containing nanoparticles or nanoclusters comprise silver-containing particles and the nanoparticles comprise iron-containing particles. Preferably, the modifying the surface comprises depositing a layer comprising an additive on the surface. Preferably, the additive is an iron-containing material. The method could further comprise heating the metal ions in an aqueous solution to produce metallic colloids. Preferably, the reducing agent is a citrate or a borohydride. More preferably, the heating is in a temperature range of about 60 to 100 degrees C.

Yet other embodiments of the invention relate to a method comprising contacting metal ions with a reducing agent to form metal-containing nanoparticles or nanoclusters and modifying a surface of the metal-containing nanoparticles or nanoclusters such that the surface comprises a hydrophobic coating. Preferably, the hydrophobic coating comprises a cationic polymer or an anionic polymer. Preferably, the hydrophobic coating comprises an alkyl chain. Preferably, the metal-containing nanoparticles or nanoclusters comprise silver particles and the modifying the surface of the metal-containing nanoparticles or nanoclusters comprise coating the silver particles with a layer of gold and adsorbing an alkyl thiol to form the hydrophobic coating. Preferably, the hydrophobic coating comprises a functional group to produce hydrogen bonding or ion-pairing. Preferably, the step of modifying the surface of the metal-containing nanoparticles or nanoclusters comprise coating the metal-containing nanoparticles or nanoclusters with a silica layer and bonding an organic molecule to the silica layer to form the hydrophobic coating. Preferably, the step of bonding of the organic molecule to the silica layer comprising bonding through a silanol group. Preferably, the step of modifying the surface of the metal-containing nanoparticles or nanoclusters comprise adsorbing oppositely charged polymer layers on the metal-containing nanoparticles or nanoclusters to form the hydrophobic coating. Preferably, the step of adsorbing oppositely charged polymers comprises depositing a positively charged polymer layer and depositing a negatively charged polymer layer. Preferably, the positively charged polymer layer comprises polyethyleneimine or polyallyalamin and the negatively charged polymer layer comprises polyacrylic acid or polystyrenesulfate. The method could further comprise removing free polymer in a solution the metal-containing nanoparticles or nanoclusters by centrifugation.

Yet other embodiments of the invention relate to a method comprising contacting metal ions with a reducing agent to form metal-containing nanoparticles or nanoclusters and modifying a surface of the metal-containing nanoparticles or nanoclusters such that the surface comprises a compound having a specific interaction with an analyte. Preferably, the compound comprises a material that is selected from the group consisting of an oligo-nucleic acid strand, a ligand, an antigen, an antibody and combinations thereof. The method could further comprise modifying the metal-containing nanoparticles or nanoclusters by a thiol chemistry to attach a metal chelating group to the surface. Preferably, the specific interaction comprises covalent bonding, hydrogen bonding, or antibody-antigen interaction. Preferably, the step of modifying the surface of the metal-containing nanoparticles or nanoclusters comprises coupling the metal-containing nanoparticles or nanoclusters to a reactive molecule or polymer that forms a covalent bond with the analyte, wherein the analyte contains a functional group.

Yet other embodiments of the invention relate to a method comprising contacting a SERS active particle with an analyte and creating an electrostatic interaction between the SERS active particle and the analyte, wherein a surface of the SERS active particle carries a positive charge. The method could further comprise modifying the surface such that the surface carries a positive charge. Preferably, the surface comprises an additive comprising a material selected from the group consisting of positively charged ions, a thiol-containing compound, a polymer and nanoparticles. The method could further comprise coating the SERS active particle with a layer comprising an additive. Preferably, the additive is an iron-containing material.

Yet other embodiments of the invention relate to a method comprising contacting a SERS active particle with an analyte and creating a hydrophobic interaction between the SERS active particle and the analyte, wherein a surface of the SERS active particle has a hydrophobic coating. A method could further comprise modifying a surface of the SERS active particle such that the surface comprises a hydrophobic coating. Preferably, the hydrophobic coating comprises an alkyl chain or a functional group to produce hydrogen bonding or ion-pairing. Preferably, the step of modifying the surface of the SERS active particle comprise coating the SERS active particle with a silica layer and bonding an organic molecule to the silica layer to form the hydrophobic coating. Preferably, the. step of modifying the surface of the SERS active particle comprise adsorbing oppositely charged polymer layers on the SERS active particle to form the hydrophobic coating. Preferably, the step of adsorbing oppositely charged polymers comprises depositing a positively charged polymer layer and depositing a negatively charged polymer layer. Preferably, the hydrophobic interaction comprises van der Waals interaction.

Yet other embodiments of the invention relate to a method comprising contacting a SERS active particle with an analyte and creating a specific interaction between the SERS active particle and the analyte, wherein a surface of the SERS active particle comprises a compound having a specific interaction with the analyte. Preferably, the compound comprises a material that is selected from the group consisting of an oligo-nucleic acid strand, a ligand, an antigen, an antibody, and combinations thereof. The method could further comprise modifying the SERS active particle by a thiol chemistry to attach a metal chelating group to the surface. Preferably, the specific interaction comprises covalent bonding, hydrogen bonding, or antibody-antigen interaction. The method could further comprise coupling the SERS active particle to a reactive molecule or polymer that forms a covalent bond with the analyte, wherein the analyte contains a functional group. Preferably, the specific interaction comprises interaction of biotin-streptavidin or DNA/RNA strands.

Preferably, the SERS active particles comprise a metal. Preferred metals include gold, silver, copper, lithium, sodium, potassium, palladium, platinum, and aluminum. The SERS active particles may also preferably include composite-organic-inorganic-nanoparticles (COINs). Preferred COINs include adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

In the practice of the present invention, the Raman spectrometer can be part of a detection unit designed to detect and quantify metallic colloids of the present invention by Raman spectroscopy. Methods for detection of Raman labeled analytes, for example nucleotides, using Raman spectroscopy are known in the art. Variations on surface enhanced Raman spectroscopy (SERS), surface enhanced resonance Raman spectroscopy (SERRS) and coherent anti-Stokes Raman spectroscopy (CARS) are also known and are included within the present invention.

A non-limiting example of a Raman detection includes an excitation beam that is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the flow path and/or the flow-through cell. The Raman emission light from the COINS or analytes adsorbed on silver colloids is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector that includes an avalanche photodiode interfaced with a computer for counting and digitization of the signal.

Another example of a Raman detection unit is includes a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm, a light emitting diode, an Nd:YLF laser, and/or various ions lasers and/or dye lasers. The excitation beam may be spectrally purified with a bandpass filter (Corion) and may be focused on the flow path and/or flow-through cell using a 6X objective lens (Newport, Model L6X). The objective lens may be used to both excite the analyte and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection in the methods of the present invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In certain aspects of the invention, a system for detecting an analyte of the present invention includes an information processing system. An exemplary information processing system may incorporate a computer that includes a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used. The information processing and control system may further comprise any peripheral devices known in the art, such as memory, display, keyboard and/or other devices.

In particular examples, the detection unit can be operably coupled to the information processing system. Data from the detection unit may be processed by the processor and data stored in memory. Data on emission profiles for various Raman labels may also be stored in memory. The processor may compare the emission spectra from the sample in the flow path and/or flow-through cell to identify the Raman-active organic compound. The processor may analyze the data from the detection unit to determine, for example, the sequence of a polynucleotide bound by a silver colloid employed by the methods of the present invention. The information processing system may also perform standard procedures such as subtraction of background signals While certain methods of the present invention may be performed under the control of a programmed processor, in alternative embodiments of the invention, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages may be used to analyze the data obtained from the detection unit. In alternative embodiments of the invention, data analysis may be performed, using an information processing system and publicly available software packages.

FIG. 1 shows the general steps involved for obtaining Raman spectra of analytes by modifying SERS nanoparticles (top view) and surfaces (bottom view). While the analyte molecules absorbed (or attached) to single modified nanoparticles can give SERS signal, the addition of a coagulant such as LiCl, NaCl or other salts can cause the nanoparticles to aggregate to generate much stronger Raman signals. Thus, a coagulant is used in case the analyte molecules do not cause significant aggregation.

The concentration of the analyte can be determined by comparing the peak ratios of known reference compounds over a variety of concentrations to the actual peak ratio of the analyte. Accurate identification of the analyte can be accomplished utilizing the analyte's Raman spectra. Once the analyte is identified, similar reference compounds can be determined for the comparison.

Preferably a library of peak is maintained for a variety of reference compounds over a range of concentrations. Instead of reference compounds, the analyte peak ratios can be directly compared to the known peak ratios for the analyte at a variety of concentrations if these peak ratios are available.

The embodiments of the invention present several approaches to modify the substrate surface in order to facilitate analyte absorption. The inventors have demonstrated the feasibility to generate positively charged silver particles by adsorption of cationic polymers. The inventors have developed methods for preparing silver and gold particles reproducibly. The inventors have also developed methods to coat silver and gold particles with silica which can be derivatized with various molecules using well-known silanol chemistry.

Certain embodiments of the invention concern methods for coating porous substrates with a uniform layer of one or more metals, such as Raman active metals. For example, the porous substrates could be porous silicon substrates. Any porous substrate that is resistant to the application of heat may be used in the disclosed methods, systems and/or apparatus. In certain embodiments, application of heat to about 300° C., 400° C., 500° C., 600° C., 700° C., 800° C., 900° C. or 1,000° C. is contemplated. In some embodiments of the invention, the porous substrate may be rigid. A variety of porous substrates, including but not limited to porous silicon, porous polysilicon, porous metal grids and porous aluminum, are could be used in the embodiments of the invention. Exemplary methods of making porous substrates are disclosed in further detail below.

Porous polysilicon substrates may be made by techniques such as the following. A layer of porous polysilicon may be formed on top of a semiconductor substrate by the use of low pressure chemical vapor deposition (LPCVD). The LPCVD conditions may include, for example, a pressure of about 20 pascal, a temperature of about 640° C. and a silane gas flow of about 600 sccm (standard cubic centimeters). A polysilicon layer may be etched, for example using electrochemical anodization with HF (hydrofluoric acid) or chemical etching with nitric acid and hydrofluoric acid, to make it porous. Typically, porous polysilicon layers formed by such techniques are limited in thickness to about 1 μm (micrometer) or less. In contrast, porous silicon can be etched throughout the thickness of the bulk silicon wafer, which has a typical thickness of about 500 μm.

Porous aluminum substrates may also be made by other techniques. For example, nanoporous aluminum oxide thin films may be fabricated on silicon or silicon dioxide using an electrochemical-assisted self-assembly process. The porous aluminum film may be thermally annealed to improve its uniformity. Alternatively, a thin layer of solid aluminum may be electrochemically anodized in dilute solutions of oxalic acid and/or sulfuric acid to create a nanoporous alumina film. The examples disclosed herein are not limiting and any known type of heat resistant porous substrate may be used. Such porous substrates may be uniformly impregnated with one or more metals, such as silver, using the methods disclosed herein.

The SERS substrate surface can be modified in various ways to improve one or more type of interactions between the analyte molecules and the modified surface, as summarized below.

Electrostatic interaction: Silver and gold nanoparticles prepared by reduction of the metal ions with common reducing agents such as citrate and sodium borohydride have negative surface charges primarily due to the adsorption of major anions (citrate or $BH_4^-$) in solution. Those negatively charged nanoparticles can be used directly for analyzing most positively charged molecules as the strong electrostatic attraction brings the analyte molecules close to the particle surface. However, for analyzing negatively charged molecules, low SERS signal intensity is expected unless the electrostatic repulsion is overwhelmed by specific interactions between the molecules and the surface. To overcome this difficulty, the nanoparticles surface can be made to carry positive charges by various means as summarized in Table 1.

TABLE 1

Examples of charge reversal of negatively charged particles to positively charges particles. The same principles could apply for converting positively to negatively charged particles.

| Methods | Additives | Examples |
|---|---|---|
| Adsorption | Simple ions (e.g., protons (pH) & ferric ions) | Coating silver particles with ferric ions in acidic solution. |
| | Small molecules (e.g., thiol amines) | Thiol amines can adsorb strongly on gold surface and make the particle positively charged in neutral solution. |

TABLE 1-continued

Examples of charge reversal of negatively charged particles to positively charges particles. The same principles could apply for converting positively to negatively charged particles.

| Methods | Additives | Examples |
|---|---|---|
| Deposition | Polymers (e.g., polyallylamine or polyethyleneimine) | Mixing silver particles with polyethyleneimine led to a stable suspension with positive charge density |
| | Very fine nanoparticles (e.g., iron oxides) | Hematite particles (<10 nm) adsorb readily on silver particles. |
| | A thin layer of inorganic phase (e.g., hematite or titanium oxide) | Coating with a thin layer of hematite which makes the surface positive at pH <7. |

Figure 2:
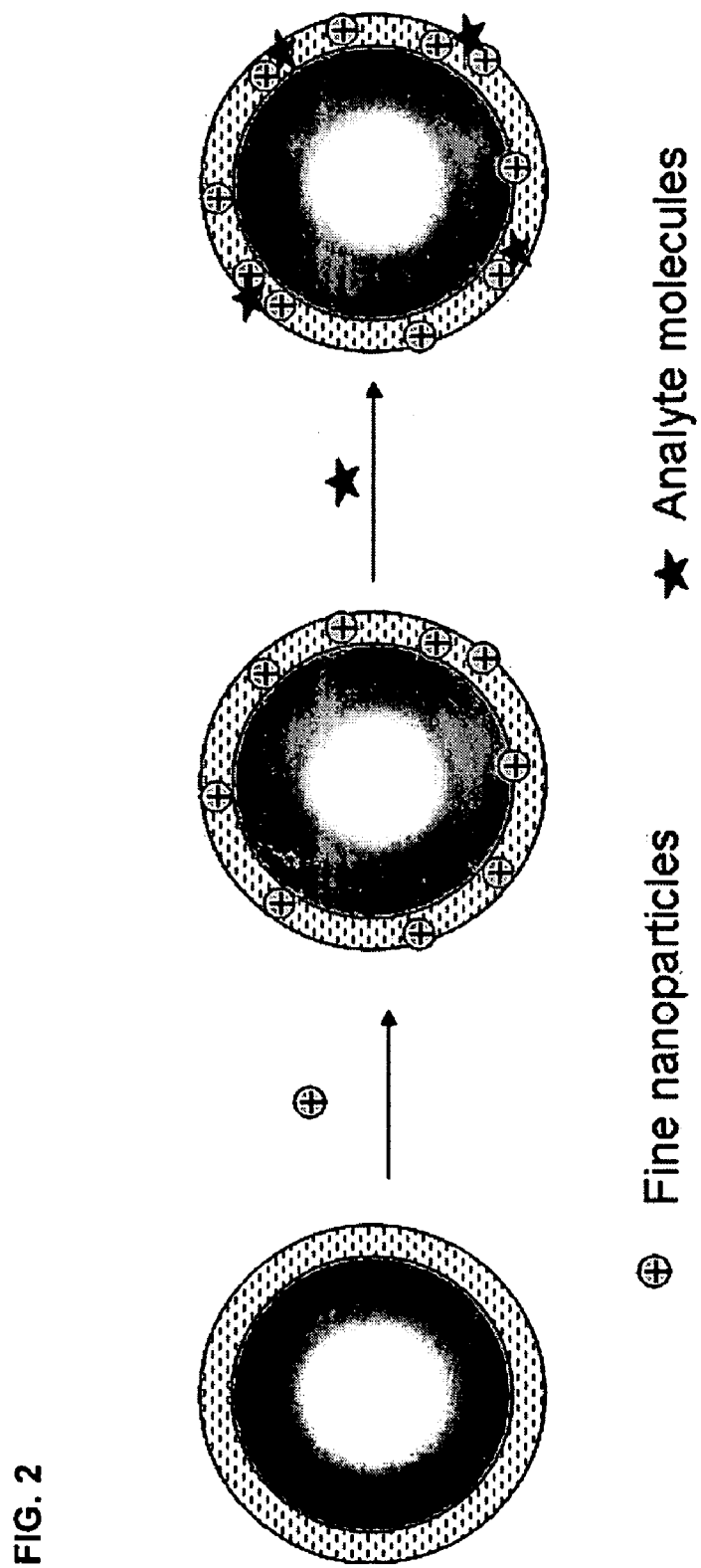
FIG. 2 illustrates an embodiment of the invention wherein a SERS active particle is coated with an adsorbed layer of positively charged nanoparticles that enhance the adsorption of an analyte molecule to the SERS active particle.

FIG. 2 illustrates some embodiments of the invention for creating a positively charged SERS particles by using relatively small positively charged nanoparticles (such as $Fe_2O_3$ and FeOOH) as anchors for adsorption of negatively charged analytes. In particular, FIG. 2 illustrates an embodiment of the invention wherein a SERS active particle is coated with an adsorbed layer of positively charged nanoparticles that enhance the adsorption of an analyte molecule to the SERS active particle.

Figure 3:
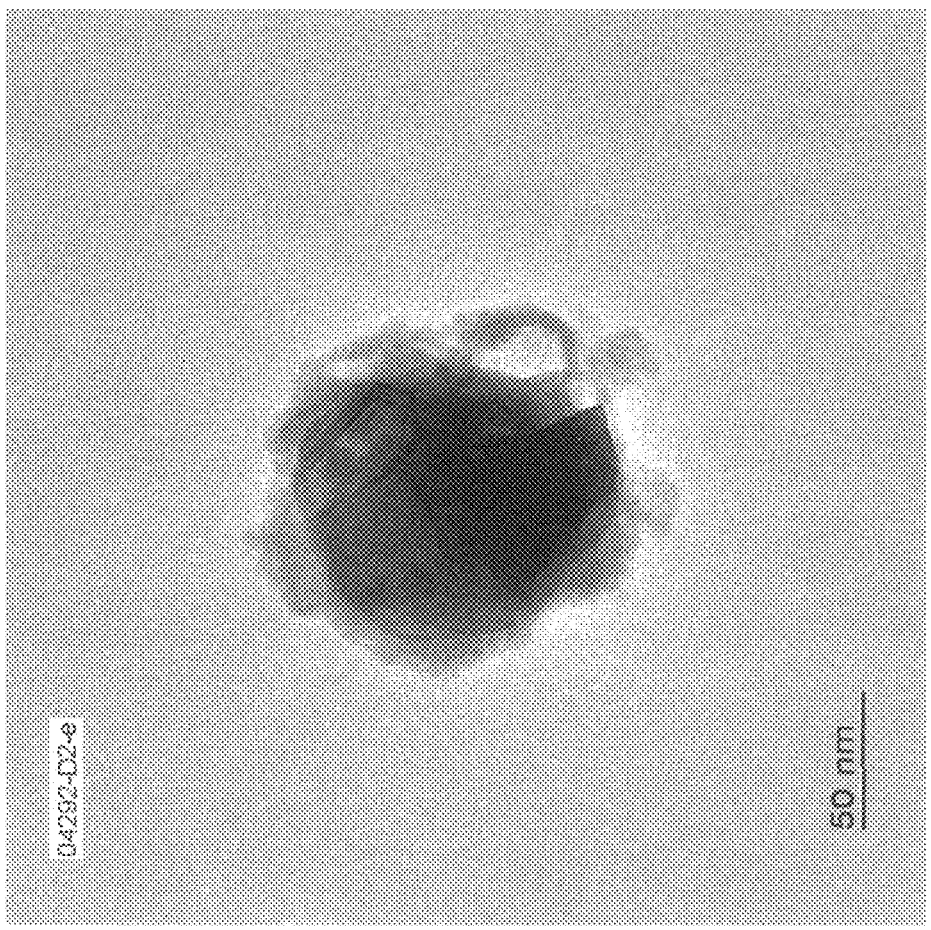
FIG. 3 shows the surface of silver particle completely covered with hematite nanoparticles as revealed by TEM.

For SERS analysis of negatively charged analytes, it is likely to be preferable to use silver particles with sub-monolayer coverage by hematite particles to allow the analyte molecules to be closer to the silver particle surface. The charge carried by the coated silver particles can be still negative. However, because of the local positive charges of hematite particles, negatively charged analyte molecules can be brought to the silver surface as shown in FIG. 2. The following procedure can be used to prepare silver particles with different degree of surface coverage by hematite particles. Dilute the hematite suspension (1 mM $Fe_2O_3$) 100 to 1000 times with 1 mM HCl. Mix equal volume of the diluted hematite suspension with SERS Ag at 1 mM. Add analyte solutions to the mixtures. After incubating for fixed period time (1 to 15 min), measure the Raman intensity. If no aggregation takes place, 100 mM NaCl or other electrolytes may be added to induce particle aggregation in order to increase the SERS signal. Alternatively, Hematite suspension may be mixed with analyte solutions first before mixing with SERS silver particles. The surface of a silver particle is substantially completely covered with hematite nanoparticles as revealed by the TEM shown in FIG. 3, wherein the black particle represents a silver particle and strip-like coating represents hematite.

Figure 4:
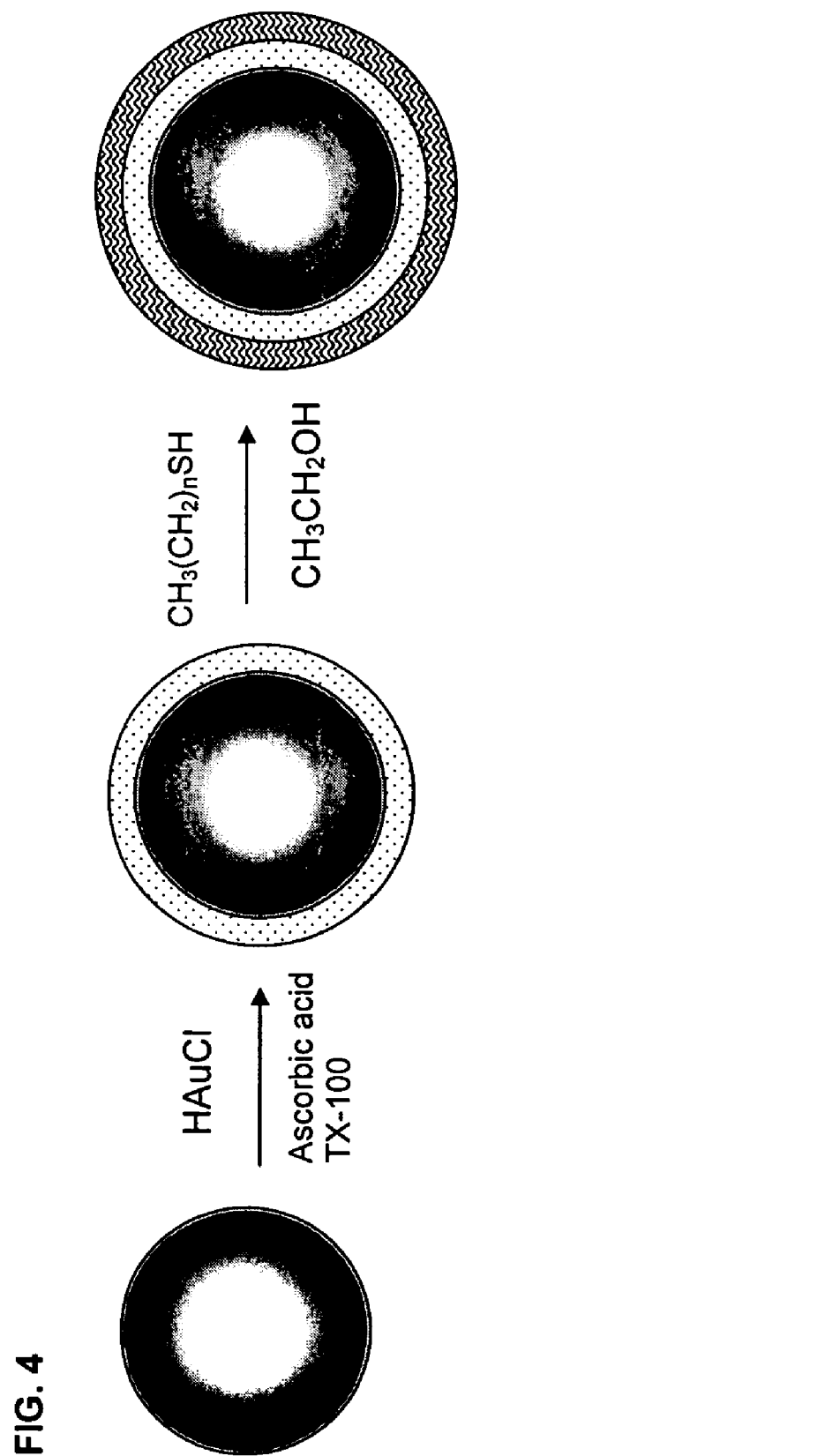
FIG. 4 illustrates an embodiment of the invention wherein a silver particle is first coated with a layer of gold before adsorption of alkyl thiol to form a hydrophobic layer.

Hydrophobic interaction: Most of large organic molecules of medical and environmental interest are generally at least partially hydrophobic. This is one of main reasons for the wide applicability of reverse phase HPLC as an analytical tool. An organic coating can be created on silver/gold particles to retain various analyte molecules as in the case of reverse phase chromatography. For example, alkyl chains of different lengths (from C4 to C18) can be grafted to gold particles or gold coated silver particles as shown in FIG. 4.

In other embodiments of the invention, other functional groups can also be introduced in the organic phase to include more specific interactions such as H-bonding and ion-pairing. The strong S—Au interaction can also be employed to introduce various functional groups into the hydrophobic layer around the particles. For example, bifunctional molecules of the type HS—R—X can be adsorbed on gold or gold coated silver surface, where X can be carboxyl, amine, hydroxyl, and so on, and R can be any type of hydrocarbon moiety with or without various functional groups to facilitate specific interactions with the analyte molecules. For example, the introduction of amine or positively charged ammonium groups will facilitate electrostatic interaction with negatively charged analyte molecules. Similarly, the presence of negatively charged functional groups such sulfate and phosphate can facilitate ion-pairing with positively charged analytes.

Figure 5:
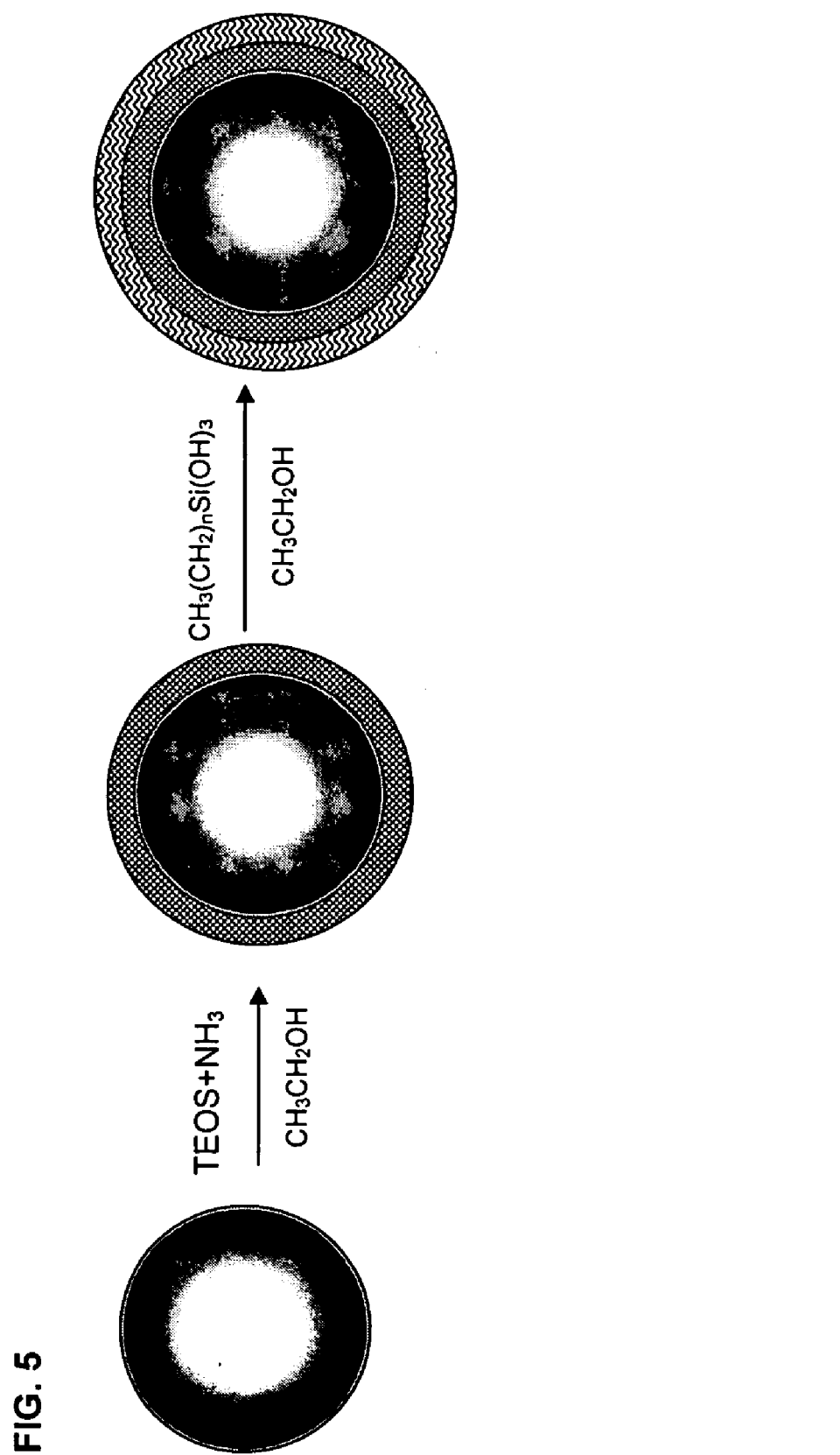
FIG. 5 illustrates an embodiment of the invention wherein a metal particle is first coated with a layer of silica before grafting organic molecules by silanol chemistry.

Alternatively in other embodiments of the invention, the metal nanoparticles can be coated with a thin layer of silica and then various organic molecules can be attached through the silanol groups as shown in FIG. 5.

In one embodiment of the invention, silver and gold particles can be coated with a layer of silica by using a modified Stober process which was originally developed to produce silica spheres. In a 50 mL plastic centrifuge tube, add 15 mL of ethanol, 80 uL of 10% tetraethylorthosilicate (TEOS) in ethanol and 4 mL of SERS silver particles at total silver concentration of 10 mM. Mix the solution well before adding 0.5 mL 28% ammonium hydroxide to initiate the hydrolysis of TEOS. After 60 min, divide the suspension into two 50 mL centrifuge tubes in equal volume (10 mL). Add 30 mL of 1 mM $Na_3$Citrate to each tube. Centrifuge at 4500 g for 15 min with a swing-bucket rotor. Withdraw and discard the supernatant. Store the silica coated silver particles in ethanol or in an aqueous solution at low ionic strength and pH<7.5 (such as 0.1×PBS buffer at pH=7.4). Examination under TEM showed that the silver particles (shown as the black regions) are substantially coated with silica (shown as gray coating on the black regions) having a thickness of about 5 nm as shown in the TEM photograph in FIG. 6. The thickness of the silica coating can be controlled by varying the particle concentration or total surface area. Thinner silica coatings can be achieved by adding of more silver particles. If the concentration of the original silver suspension is too low, centrifugation may be used to concentrate the particles before coating. A similar procedure can also be applied to coat gold or gold-coated silver particles.

According to the embodiments of the invention there are numerous ways to ionize the silica surface. One facile approach is to use silane compounds of the type, X—R—Si(OCH$_3$)$_3$ or X—R—Si(OCH$_2$CH$_3$), where R can be alkyl or any hydrocarbon moiety with or without functional groups, X can be H or various functional groups such as —COOH, —NH$_2$, —N(CH$_3$)$_3^+$, etc. Organic solvent such as ethanol may used to dissolve the silane compounds before silica coated silver or gold particles are added.

Figure 7:
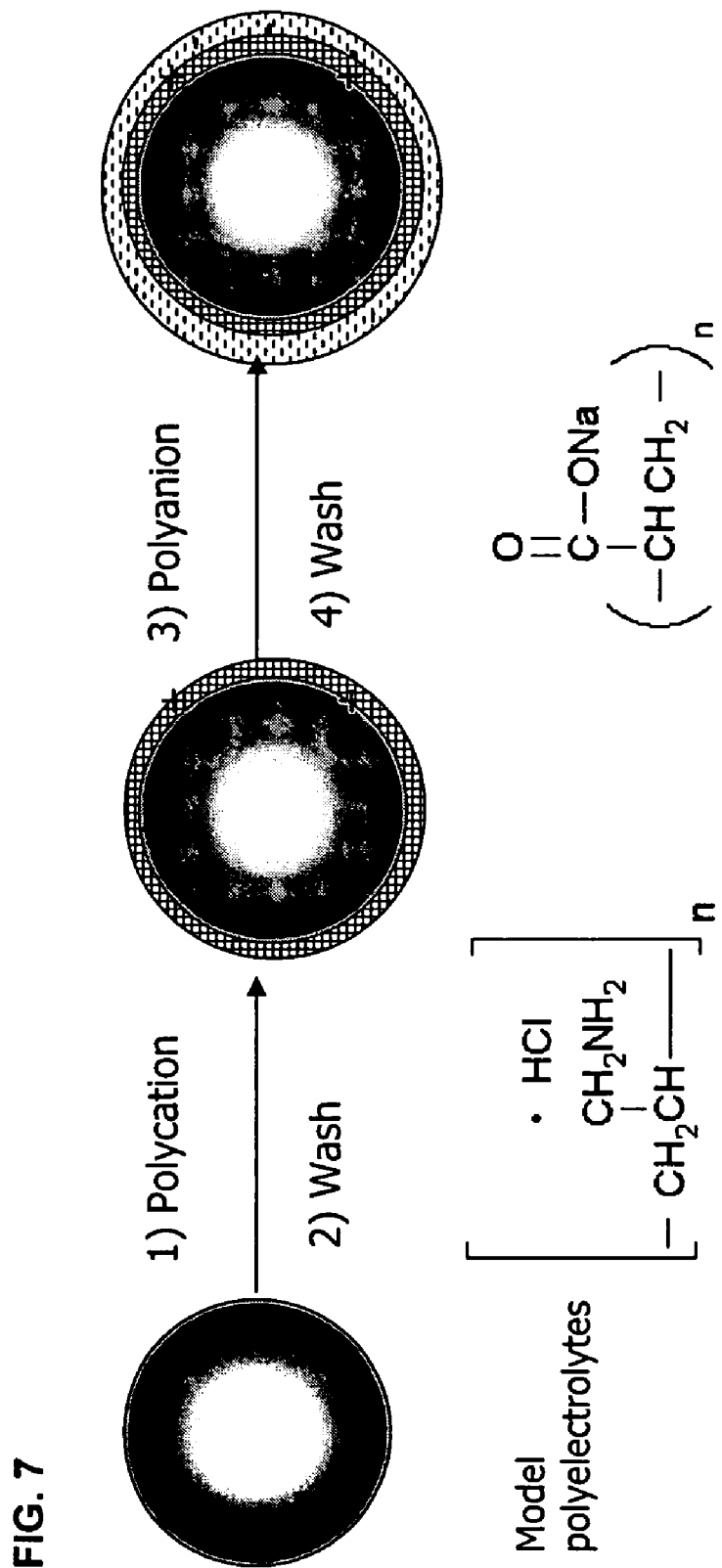
FIG. 7 illustrates an embodiment of the invention wherein a metal particle is coated layer-by-layer with various functional groups by alternate adsorption of oppositely charged polymers to form a hydrophobic layer.
Figure 8:
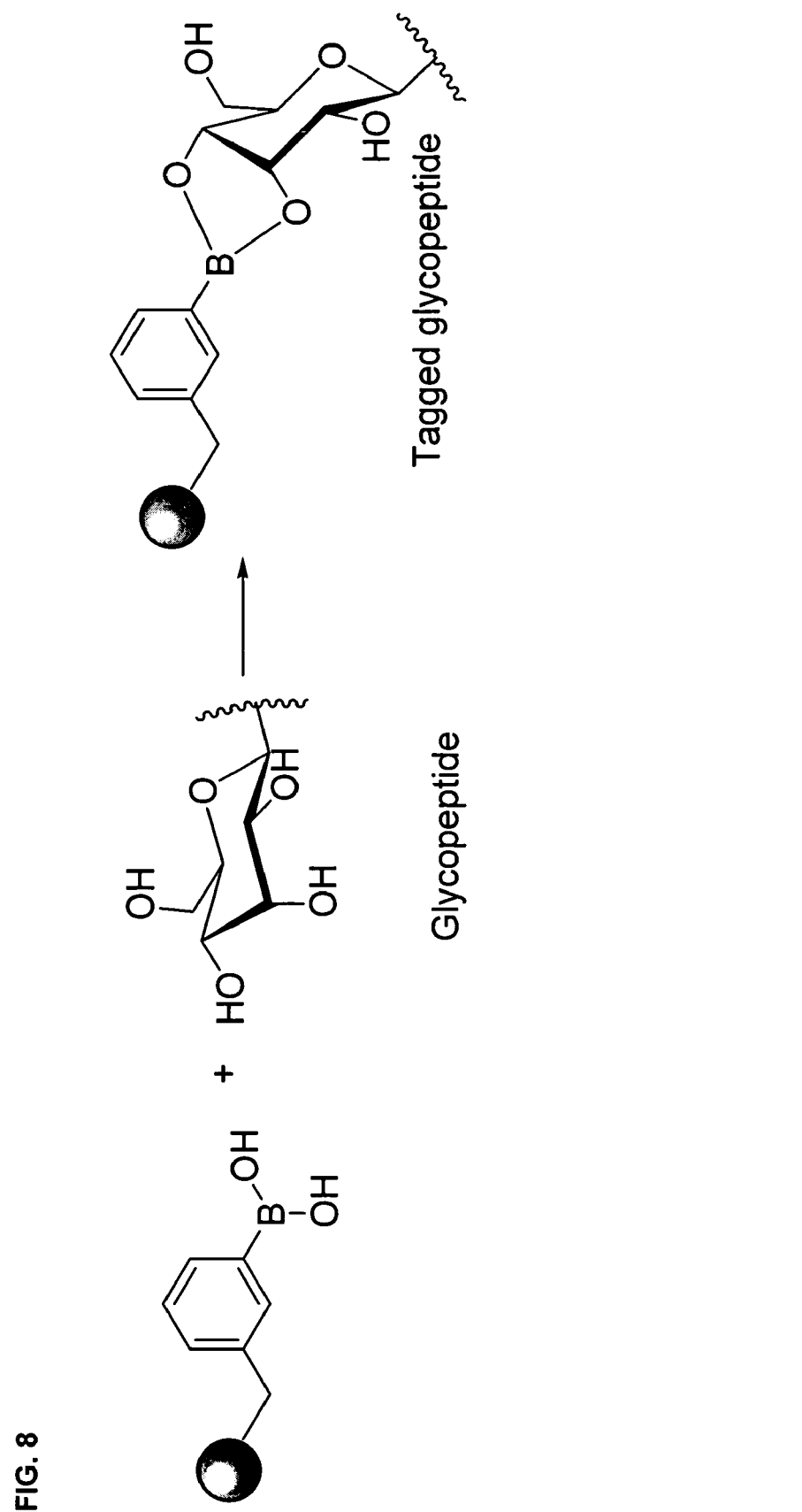

Yet in other embodiments of the invention, layer by layer (LBL) adsorption of oppositely charged polymers can also be used to create a very stable organic layer with various functional groups from the polymers as shown in FIG. 7. FIG. 7 shows the structure of two model polyelectrolytes, polyallylamine and polyacrylic acid. Other cationic and anionic polymers with suitable solubility can also be used to create multiply layers of polymer coating. Usually, two types of polymers, one cationic, the other anionic, are sufficient to create the coating of any desirable thickness. However, more types of polymers can be used so that the desired ional groups can be introduced at certain distance from the native metal surface.

Specific interaction: Covalent bonding and other strong specific interactions such as hydrogen bonding between complimentary oligonucleic acid strands as well as antibody-antigen interaction can be used to bring the analyte molecules very close to the native or derivatized metal particle surface. For example, when analyzing thiol-containing compounds, gold nanoparticles or silver particles with a thin gold layer can be used as a SERS substrate to take the advantage of the strong S—Au interaction.

In other embodiments, the SERS particles can also be coupled with certain reactive molecules or polymers which can form covalent bonds with analytes containing given functional groups. For example, there are several functional groups that can be used to attach an analyte to the particle surface. One such example is an epoxide. A polymer containing epoxide groups can be adsorbed on to the surface of the nanoparticle by adding a concentrated nanoparticle suspension to a large volume of the polymer solution. A good starting point is to add one volume of the nanoparticle suspension to four volumes of the polymer solution. The excess polymer is then removed by centrifugation and the modified particles are resuspended in the desired medium. An analyte containing amine groups can be reacted with this polymer at an alkaline pH resulting in the formation of a secondary amine bond.

Figure 8:
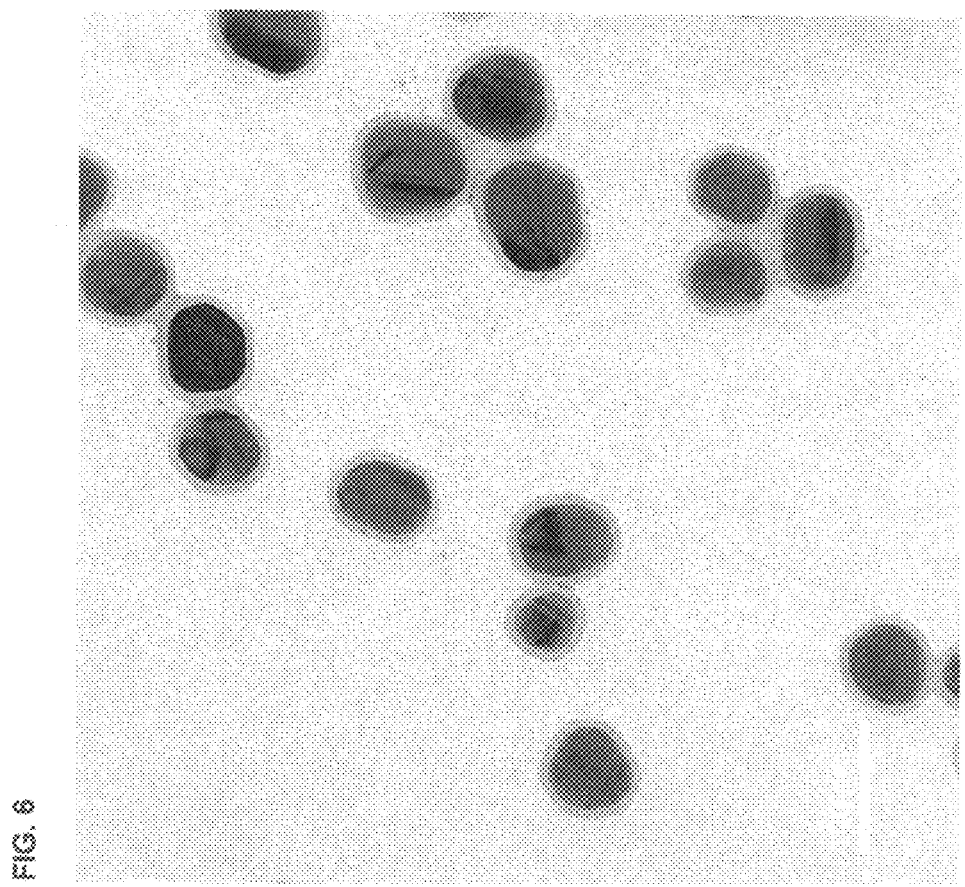
FIG. 8 illustrates an embodiment of the invention wherein a metal particle having an affinity ligand captures an analyte molecule, particularly, a glycopeptide molecule.

In yet other embodiments of the invention relating to analyzing proteins or peptides, the metal particles can be derivatized with ligands with strong affinity for the analytes, for instance, immobilized metal affinity chromatography (IMAC) for 6×His proteins and phosphoproteins, Glutathione for Glutathione-S-Transferase (GST)-proteins and boronic acid or lectin for glycoproteins and polysaccharides. For example, FIG. 8 shows a SERS particle with an affinity ligand for capturing a glycopeptide. FIG. 8 only illustrate one particular example of affinity ligands. Other ligands could also be used, for example, boronic acid can be used for analyzing glycopeptite, glycoprotein as well as carbohydrates.

In one example, the nanoparticles can be modified by using thiol chemistry to attach a metal chelating group to the nanoparticle surface. A compound containing both a thiol group and a metal chelating group such as NTA (nitrilotriacetic acid) is dissolved in an appropriate solvent (e.g., water or ethanol) and the nanoparticles are then added to this solution. The resulting mixture is allowed to equilibrate for up to 12 hours, after which the nanoparticles are then washed by centrifugation. The desired metal is then added to the modified nanoparticles. For the capture of phosphopeptides or proteins, iron (III) is commonly used. The modified nanoparticles are suspended in a dilute solution of iron (III) chloride at acidic pH. After equilibration, the excess iron solution is removed by centrifugation and the iron-loaded particles are resuspended in an acidic buffer. The phosphopeptide is then introduced to the iron-loaded particles and allowed to equilibrate. The phosphate forms a complex with the iron on the nanoparticle surface and thus should be close enough to the metal surface to obtain a strong surface-enhanced Raman signal.

In other embodiments of the invention, the SERS substrate can also be first conjugated with the antigens/antibodies for a given protein to be analyzed. For example, antibodies can be conjugated to the nanoparticle surface using N-hydroxysuccinimide (NHS) chemistry. The nanoparticle surface is first modified by mixing with a compound containing a thiol group at one end and a carboxylic acid on the other. The compound attaches to the nanoparticle surface via the thiol group, leaving the carboxylic acid as the exposed functional group. This carboxylic acid is then converted to an NHS-ester, and resulting particles are washed and then mixed with the antibody. The amine groups of the antibody react with the NHS-ester to form an amide bond, thus creating antibody-labeled nanoparticles. Alternatively, protein A can be adsorbed onto the nanoparticle surface and then used to bind the antibody of choice. This prevents the need for developing a separate nanoparticle for each specific antibody.

In other embodiments of the invention relating to analyzing DNA or oligo-nucleic acids, the SERS particles can be first derivatized with a segment of complimentary oligo-nucleic acids. For example, derivatization can be done by incubating the nanoparticles with a disulfide-protected oligonucleotide overnight. Sodium chloride is then gradually added over time to allow for maximal coverage of the nanoparticle surface with the highly-charged oligonucleotide. Great care must be taken to avoid aggregation of the nanoparticles by too large of an increase in the salt concentration. Unbound oligonucleotides can be removed by centrifugation and the pellet resuspended in a buffer with the desired sodium chloride concentration.

In the above cases, the Raman scattering from the affinity ligands should preferably be subtracted as follows. A background Raman spectrum of each modified particle in the absence of any analyte is recorded. Upon collection of a spectrum in the presence of analyte, the background spectrum is then subtracted out yielding peaks that can be attributed to the analyte in question. This can be done using a variety of commercially-available software. An examination of the change in background peaks can also provide information about the binding mode of the analyte. Changes in particular bands can be associated with functional groups in the background and indicate how the analyte is interacting with the nanoparticle. This is useful in fine-tuning the specificity of the nanoparticle for a particular analyte.

Some SERS particles of the embodiments of the invention are shown in Table 2.

TABLE 2

Examples for derivatizing the SERS substrate with reactive groups for covalently binding analyte molecules containing specific functional groups

| Functional Groups in analyte molecules | Reactive groups on SERS substrate |
|---|---|
| Amine | N-Hydroxysuccinimide ester, Isothiocyanates, sulfonyl halides |
| Thiol | Maleimide, Haloacetyl |

EXAMPLE 1

Preparation of Silver Colloids

To a 250 mL round bottom flask equipped with a stirring bar, was added 100 mL de-ionized water and 0.200 mL of a 0.500 M silver nitrate solution. The flask was shaken to thoroughly mix the solution. 0.136 mL of a 0.500 M sodium citrate solution was then added to the flask using a 200 μl pipette. The flask was then placed in a heating mantle and the stirrer was set at medium speed. A water cooled condenser was attached to the flask and heating commenced. The heating mantle was applied at maximum voltage, resulting in boiling of the solution between 7 and 10 minutes. Color changes occur within 120 seconds of boiling. The heating is stopped after 60 minutes, the solution is cooled to room temperature and the resulting colloidal suspension is transferred to a 100 mL glass bottle for storage.

EXAMPLE 2

Preparation of Fine Hematite Particles

Hematite nanoparticles with an average diameter <10 nm can be prepared by heat forced hydrolysis of ferric ions using the following procedure. ACS Reagent grade chemicals and de-ionized (DI) water (with resistance about $1 \times 10^5$ $\Omega cm^{-1}$) should be used. Prepare 1.00M $FeCl_3$ solution by dissolving $FeCl_3.6H_2O$ (Sigma-Aldrich) into 4.00 mM HCl. Filter the solution through 0.22 μm Millipore filter before use. In a 250 mL media bottle (Pyrex) with a magnetic. stirrer, add 100 mL of DI water, 0.4 mL of 1N HCl. Heat the solution on a hot place stirrer to boiling. Under vigorous stirring, add 2.00 mL of filtered 1M $FeCl_3$ solution rapidly. Sixty seconds after the addition, cap the media bottle and place the bottle into an oven set at 95° C. The particle size depends on the heating time in oven. In general, longer heating time led to larger particles. Less than 10 nm particles will be obtained when the oven heating time is less than 60 min. The hematite particles so prepared have a positive zeta potential at pH<9.

EXAMPLE 3

Coating SERS Ag with Fine Hematite Particles

To coat silver particles completely with hematite nanoparticles, in a 1 mL centrifuge tube, add 0.9 mL of 8 nm Hematite suspension (1 mM as $Fe_2O_3$, particle number concentration is $1 \times 10^{14}$/mL). Add rapidly 100 μL of SERS silver particles (about 50 nm) with a total silver concentration of 1 mM (particle concentration is about $2 \times 10^{11}$ particles/mL). Shake the suspension immediately to have uniform mixing. Centrifuge at 6000 g for 60 min. Withdraw with a pipette and discard the supernatant as much as much as possible. Re-suspend the coated Silver particles in 1 mM HCl. Under these preparation conditions, the surface of silver particles is completely covered with hematite nanoparticles as revealed by TEM shown in FIG. 3.

EXAMPLE 4

Coating Silver Particles with a Thin Layer of Gold

Prepare stock solutions of 0.100 M of gold (III) chloride, 0.100M of ascorbic acid and 1.00M of TX-100 (Poly(oxyethylene) iso-octylphyl ether) by dissolving appropriate amounts of the Reagent grade chemicals in DI water. Filter the stock solutions through 0.22 uM Millipore filter. Fresh ascorbic acid should be prepared regularly and should be kept at 4° C. To coat SERS silver with a layer of gold, the following procedure can be used.

In 125 mL media bottle, add 30 ml of DI water, 0.5 mL of $HAuCl_4$ stock solution, 0.6 mL of ascorbic acid solution and 1 mL of TX-100. Mix the solution well before adding 68 mL of SERS Ag. Cap the bottle and shake the solution vigorously. Let the bottles sit at room temperature for 60 min while the solution is agitated with a magnetic stirrer. The coating thickness is about 5 nm. The thickness of gold layer can be controlled by changing the amount of SERS silver used. The amount of water should be adjusted so that the final volume of solution remains at 100 mL.

EXAMPLE 5

Grafting Alkyl Chains to Gold or Gold Coated Silver Particles

For alkyl thiols with less than 6 carbons, the coating can be preceded in aqueous solution containing lmM sodium citrate (to maintain the pH and to stabilize gold colloids) and 1 mM alkyl thiols. Gold and gold coated silver nanoparticles will be equilibrated with the thiol solution for 24 hours to allow adsorption of thiol molecules. For alkyl thiols of greater length, an organic solvent such as ethanol needs to be used to prepare the thiol solution at 1 mM. 24 hr of incubation is needed to allow the thiol molecules to form a self-assembled monolayer on the gold particle surface. This procedure also applies to alkyl thiols with a shorter chain (<C6) and other thiol containing compounds which can be dissolved in ethanol and other suitable organic solvents.

EXAMPLE 6

Preparation of Layer by Layer Coated SERS Particles

A very stable organic coating can be formed by adsorption of multiple layers of oppositely charged polyelectrolytes. This layer by layer (LBL) approach can be applied to successfully coat colloidal particles. For example, first coat the negatively charged silver particles with a polycation (e.g., polyethyleneimine or polyallylamine). Remove free polymers in solution by centrifugation. Then, apply a negatively charged polymer (such as polyacrylic acid and sulfate-modified polystyrene). Remove the free polymers again by centrifugation before applying the next layer of cationic polymer. The process continues until the organic layer reaches the desired thickness. As a result of the strong electrostatic interaction, the polymer layers are very stable against desorption. Various functional groups can be incorporated into the organic coating layer by using different types of polymers or copolymers.

EXAMPLE 7

Specific Interaction Between Thiol-Containing Analyte and Au or Ag Nanoparticles A solution of thiol-containing analyte is added to a colloidal suspension of gold nanoparticles or gold-coated silver nanoparticles. Incubation time of this analyte with the colloid can be varied to allow for the sample to equilibrate. Full equilibration leading to the formation of a monolayer of thiol on the gold surface can take up to 12 hours. The nanoparticles are then induced to aggregate by the addition of a salt solution and the surface-enhanced Raman spectrum acquired.

The SERS nanoparticles or nanoclusters of the embodiments of the invention can be modified according to the nature of analytes to produce higher signal intensity and lower detection limit. Commercial applications for the SERS nanoparticles or nanoclusters of the embodiments of the invention employing the methods described herein include environmental toxicology and remediation, biomedicine, materials quality control, food and agricultural products monitoring, anesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, telesurgery, and the like.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A surface enhanced Raman spectroscopy (SERS) active particle comprising a metal-containing particle and a cationic coating on the metal-containing particle, wherein the metal-containing particle comprises a metal selected from the group consisting of silver, gold, platinum, aluminum, an oxide of aluminum, and combinations thereof, and wherein the cationic coating comprises hematite, further comprising an analyte, an aggregate of a plurality of the metal-containing particles, wherein the metal-containing particles have the cationic coating and the analyte on the metal-containing particles, and a coagulant wherein the coagulant is a salt that causes the plurality of the metal-containing particles to aggregate.

2. The SERS active particle of claim 1, wherein the metal-containing particle comprises metallic colloids.

3. The SERS active particle of claim 1, wherein the cationic coating comprises an adsorbed additive or a deposited additive.

4. The SERS active particle of claim 3, wherein the adsorbed additive comprises a material selected from the group consisting of ions, a thiol-containing compound, a polymer and nanoparticles.

5. The SERS active particle of claim 4, wherein the nanoparticles comprise an iron-containing material.

6. The SERS active particle of claim 1, wherein the SERS active particle has as planar or curved surface.

7. The SERS active particle of claim 1, wherein the SERS active particle carries a positive charge.

8. The SERS active particle of claim 1, wherein the analyte comprises m-RNA, r-RNA, t-RNA, DNA, DNA-RNA duplexes, peptide nucleic acids (PNA), restriction enzymes, activators, repressors, nucleases, polymerases, histones, repair enzymes, or chemotherapeutic agents.

9. The SERS active particle of claim 1, wherein the salt is LiCl or NaCl.

* * * * *